United States Patent
Genne et al.

(12) 
(10) Patent No.: US 6,528,524 B2
(45) Date of Patent: *Mar. 4, 2003

(54) PHARMACEUTICAL COMPOSITIONS CONTAINING CINCHONINE DICHLORHYDRATE

(75) Inventors: Philippe Genne, Talant (FR); Houssam Ibrahim, Veyrier (CH)

(73) Assignee: Debiopharm SA, Lausanne (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/424,943
(22) PCT Filed: Jun. 8, 1998
(86) PCT No.: PCT/FR98/01166
§ 371 (c)(1), (2), (4) Date: Feb. 23, 2000
(87) PCT Pub. No.: WO98/56383
PCT Pub. Date: Dec. 17, 1998

(65) Prior Publication Data
US 2002/0091136 A1 Jul. 11, 2002

(30) Foreign Application Priority Data
Jun. 11, 1997 (FR) .............................. 97 07234

(51) Int. Cl.$^7$ ................................................ A61K 31/44
(52) U.S. Cl. ....................................................... 514/305
(58) Field of Search .......................................... 514/305

(56) References Cited

U.S. PATENT DOCUMENTS 5,843,891 A * 12/1998 Sherman ...................... 514/11

FOREIGN PATENT DOCUMENTS

| WO | WO 81/03564 | 12/1981 |
| WO | WO 92/14467 | 9/1992 |

OTHER PUBLICATIONS

Janjic. <<Two–phase buffer systems with diprotic acids>>, vol. 152, pp 229–237 XP–002056486.

* cited by examiner

Primary Examiner—Jerome D. Goldberg
(74) Attorney, Agent, or Firm—Piper Rudnick LLP; Steven B. Kelber

(57) ABSTRACT

The invention relates to pharmaceutical compositions containing cinchonine dihydrochloride as active ingredient with a purity of at least 95%. The invention also relates to a process for preparing cinchonine dihydrochloride from cinchonine and the use of pharmaceutical compositions containing cinchonine dihydrochloride for treating multiple drug resistance.

4 Claims, No Drawings

PHARMACEUTICAL COMPOSITIONS CONTAINING CINCHONINE DICHLORHYDRATE

The present invention provides pharmaceutical compositions containing cinchonine dihydrochloride as active ingredient. More precisely, pharmaceutical compositions according to the invention contain cinchonine dihydrochloride with a purity of at least 95%.

The invention also provides a process for preparing cinchonine dihydrochloride.

Pharmaceutical compositions according to the invention may be used as inhibitory substances for the phenomenon called "multiple drug resistance" (MDR). In particular, pharmaceutical compositions according to the invention may be used for treating certain types of cancer-linked diseases which exhibit this MDR phenomenon.

Pharmaceutical compositions according to the invention may also be used for treating arrhythmia, as antispasmodic substances, and also in the treatment of malaria, in the event of resistance to known conventional medicaments and in association with these medicaments.

The MDR phenomenon is known in particular in connection with cancers, but it is also exhibited in the case of other diseases such as malaria. On the one hand there are cancers with innate MDR and, on the other hand, cancers with which MDR develops following treatment based on anti-cancer agents, such as anthracyclines in particular. The MDR phenomenon with cancers has the effect of inhibiting the cytotoxicity of certain anti-cancer drugs or even of rendering them ineffective.

Cinchonine is a naturally-occurring substance, extracted from the bark of quinquina, and is a member of the alkaloid family. Cinchonine has an inhibitory effect with regard to the MDR phenomenon. Its use for preparing pharmaceutical compositions intended for the treatment of cancerous tumours which develop the MDR phenomenon is described in European patent no. EP 0052608 in the name of the applicant, DEBIOPHARM SA.

Pharmaceutical compositions containing cinchonine and intended for treatment of the MDR phenomenon, however, have a certain number of disadvantages.

These disadvantages stem mainly from the fact that cinchonine is very sparingly soluble in water. This makes it difficult to administer to patients in the form of a drinkable or parenterally administered solution. Moreover, the low solubility of cinchonine in water means that its bioavailability properties are unsatisfactory with regard to oral administration. Since cinchonine is a toxic substance, with unwanted side effects, it is desirable to improve its bioavailability as this would permit a reduction in the orally administered doses and, thus, the side effects.

The applicant company has now found that a salt of cinchonine, cinchonine dihydrochloride, not only complies with the solubility and bioavailability criteria required for a pharmaceutical formulation, while maintaining the therapeutic properties required, but that it is also very stable in solution, thus favouring the formulation of aqueous preparations, in particular in an injectable form.

Furthermore, the applicant company has also noted that the bioavailability of cinchonine dihydrochloride is more constant from one patient to another. In other words, the variability of the therapeutic effect is lower when treating patients with cinchonine dihydrochloride than with cinchonine or cinchonine monohydrochloride.

The pharmaceutical composition according to the invention contains, as active ingredient, cinchonine dihydrochloride. More precisely, the pharmaceutical composition according to the invention contains cinchonine dihydrochloride with a purity of at least 95%. Cinchonine dihydrochloride in the pharmaceutical composition according to the invention preferably has a purity of at least 99%, and in particular of at least 99.9%.

In accordance with a preferred embodiment, the pharmaceutical composition provided by the invention contains cinchonine dihydrochloride combined with at least one other active ingredient compatible with cinchonine dihydrochloride and optionally at least one other pharmaceutically acceptable compound.

The other active ingredients may advantageously be chosen from the group consisting of anti-cancer agents, antimalarial agents and multiple drug resistance inhibitors.

In a non-exhaustive manner, the following may be mentioned as anti-cancer agents: doxorubicine, vinorelbine, etoposide, taxol, puromycin and, in a general manner, all cytotoxic agents involved in multiple resistance to drugs.

In a non-exhaustive manner, the following may be mentioned as antimalarial agents: quinine, chloroquinine and any other agent which induces a resistance phenomenon.

In a non-exhaustive manner, the following may be mentioned as MDR inhibitors: one or more known substances chosen from among amiodarone, quinine, quinidine, cinchonidine, verapamil, cyclosporine A, cephalosporines, biperidene, lidocaine, chlorpromazine, pentazocine, promethazine, potassium canmrenoate, amitriptyline, propanolol, demethoxyverapamil, diltiazeme, thioridazine, trifluoperazine, chloroquine, sdb-ethylene diamine, reserpine, tamoxifene, toremifene, hydrocortisone, progesterone, salbutamol and their acylated or esterified derivatives.

As another pharmaceutically acceptable compound used in compositions according to the invention, cytotoxic substances which are sensitive to the MDR phenomenon and which increase the effect of cinchonine dihydrochloride may advantageously be used.

Substances of this type are mentioned below; this list is not exhaustive in any way.

Essentially, these are hydrophobic substances, all of which have a positively charged nitrogenated group, such as, for example, vinca alkaloids, anthracyclines or similar products, epipodophyllotoxines or anti-tumour antibiotics. The following may be mentioned in particular, vincristine, vinblastine, vindesine, vinorelbine, doxorubicine, deoxydoxorubicine, tetrahydropyranyladriamycine, epidoxorubicine, aclacinomycine, demethoxydaunorubicine, daunorubicine, m-amsa, mitoxantrone, bisanthrene, demethoxydaunorubisanthrene, mithramycine, actinomycine D, puromycin, etoposide, tenoposide, emetine, ethidium bromide, cytochalasine, colchicine and taxol.

Other pharmaceutically acceptable compounds may of course be incorporated into the composition according to the invention, such as fillers, colorants, excipients, sweeteners, etc.

The optimum doses and frequency of administration of the composition according to the invention depend on the type of cancer or other disease being treated, the nature of the other active ingredients optionally used in combination with cinchonine dihydrochloride and also on the patient being treated or also on other factors that the skilled person is able to understand.

The invention thus enables an appropriate therapeutic treatment to be offered for diseases with various degrees of resistance to the classical medicaments used to treat them. In particular, thanks to the invention, there is the capacity to offer an appropriate therapeutic treatment for a number of cancerous diseases which have various degrees of resistance to anti-cancer agents. In this connection, inter alia, the following may be mentioned: acute myeloblastic leukaemia, acute lymphoblastic leukaemia, neuroblastoma, small cell lung cancer, ovarian cancer, malignant non-Hodgkinson's lymphoma and diffuse plasmacytoma. These are cancers which can involve induced MDR in response to treatment with a cytotoxic agent.

Cancers with innate MDR may also be treated. These are, for example, colonic adenocarcinoma, renal adenocarcinoma, corticosuprarenal carcinoma, pheochromocytoma, infantile sarcomas and secondary leukaemia. However, this list is not exhaustive.

Cinchonine dihydrochloride is very stable in aqueous solution and thus is suitable for preparing injectable solutions. Therefore, cinchonine dihydrochloride may be readily administered locally, near to areas to be treated, thus restricting any secondary effects in healthy parts.

The applicant company has also refined a process enabling cinchonine dihydrochloride to be obtained with a purity of at least 95%.

According to the process in accordance with the invention, cinchonine dihydrochloride is prepared by adding hydrochloric acid to cinchonine or cinchonine monohydrochloride in order to obtain cinchonine dihydrochloride and purifying the cinchonine, cinchonine monohydrochloride and/or cinchonine dihydrochloride. These stages may be performed in any sequence. Advantageously, the process for preparing cinchonine dihydrochloride according to the invention includes a final sterilising filtration stage then drying the product obtained by freeze-drying.

These purification stages are advantageously performed by high performance liquid chromatography.

According to a preferred embodiment of the process for preparing cinchonine dihydrochloride from cinchonine, the hydrochloric acid is added in two stages, the cinchonine being converted into cinchonine monohydrochloride in a first stage and then, in a second stage, the cinchonine monohydrochloride being converted into cinchonine dihydrochloride. The two neutralising stages take place at ambient temperature with constant stirring. In the first stage, the basic cinchonine is mixed with an equivalent amount of hydrochloric acid in water. If required, the mixture is heated until reaction is complete. The solution is evaporated to the saturation point for the salt and left to crystallise.

The CMH obtained is then added to a dilute solution of hydrochloric acid, with stirring. The pH is adjusted to 2.3–2.4 with hydrochloric acid, the mixture is filtered and then the solution is transferred to a plate to dry.

The cinchonine may also be neutralised to give cinchonine dihydrochloride in a single stage. The cinchonine and/or cinchonine dihydrochloride may be purified by high performance liquid chromatography.

Neutralisation by HCl is achieved using processes well known to the skilled person. Thus, hydrochloric acid may be added in small portions, with homogenisation stages between each stage.

The advantage of proceeding in small stages lies in the fact that checks can be performed during the course of manufacture, at the end of each stage, enabling better monitoring of impurities and yields.

The pharmaceutical composition according to the invention may be used to treat the phenomenon of multiple drug resistance. Thus, it may be used for treating cancers or arrhythmia or as an antispasmodic drug. It may also be used in combination with known medicaments for the treatment of malaria in the event of resistance to these medicaments.

The invention will be better understand with the help of the following non limitative examples.

EXAMPLE 1

Preparation of Cinchonine Dihydrochloride from Cinchonine Monohydrochloride 7.074 g of cinchonine monohydrochloride, obtained from FLUKA, is added to 50 ml of water, with stirring, at ambient temperature. The pH of this solution is adjusted to 2.3±0.1 after adding 19.7 ml of hydrochloric acid (1 N).

This solution is kept at ambient temperature, with stirring, for one hour until the pH is completely stable. The solution is then subjected to sterilising filtration by passage through a 0.2 μm millipore filter.

The solution is fractionated and then deep frozen at −80° C. in contact with liquid nitrogen, then freeze-dried for 70 hours. 5.86 g of freeze-dried cinchonine dihydrochloride powder are then obtained.

EXAMPLE 2

Chemical Structure and Purity of the Cinchonine Dihydrochloride Obtained in Example 1

A portion of the product obtained in example 1 above was analysed by IR spectrometry in potassium bromide, using a Perkin-Elmer model 881 IR spectrometer.

The spectrum obtained complies with the spectrum of pure cinchonine dihydrochloride.

A portion of the product obtained in example 1 was diluted with water. The sample was analysed by UV spectrometry.

The spectrum obtained complies with the spectrum of pure cinchonine dihydrochloride.

The melting point of cinchonine dihydrochloride obtained in example 1 was determined with the aid of a Kofler heating bed (Kofler Heizbank, Reichert, Germany). A value of 232±3° C. was obtained.

EXAMPLE 3

Stability of the Cinchonine Dihydrochloride Obtained in Example 1

The $^1$H and $^{13}$C spectra were built up using samples of 100 mg and 20 mg respectively in 0.5 ml of deuterated methanol.

The NMR spectra were obtained using a Bruker DRX 500 spectrometer fitted with a so-called "reversible" sensor.

The aqueous solution was kept at ambient temperature and in the light for 30 days. After 30 days, the NMR spectra were recorded in the same way as above.

The NMR spectra obtained on day 0 and day 30 are unchanged.

Cinchonine dihydrochloride thus demonstrates remarkable stability.

EXAMPLE 4

In Vivo Bioavailability of Cinchonine Dihydrochloride

Comparative tests were performed in order to demonstrate the better in vivo bioavailability of cinchonine dihydrochloride.

These tests were performed in four "Beagle" dogs, two of which were male and two female.

Each dog received, on day 1, a dose of 50 mg per kg of cinchonine dihydrochloride and, on day 8, an equivalent dose of cinchonine monohydrochloride. Blood samples were taken at regular intervals after each administration.

The results of a pharmacokinetic study are summarised in the table below:

| Animal | M1 | | M2 | | F1 | | F2 | |
|---|---|---|---|---|---|---|---|---|
| Cinchonine salt | CDH | CMH | CDH | CMH | CDH | CMH | CDH | CMH |
| Dose mg/kg | 50 | 50 | 50 | 50 | 50 | 50 | 50 | 50 |
| $C_{20}$ min | 0.23 | 0 | 2.1 | 0.25 | 2.05 | 1.04 | 3.68 | 1.66 |
| $T_{1/2}$ a (min) | 0.26 | 0.06 | 0.39 | 0.24 | 0.10 | 0.05 | 0.34 | 0.11 |

The blood concentration of cinchonine dihydrochloride 20 minutes after administration is greater than that of cinchonine monohydrochloride. Moreover, the absorption time of cinchonine dihydrochloride is also greater than that of cinchonine monohydrochloride.

These results demonstrate that cinchonine hydrochloride has improved bioavailability properties as compared with cinchonine monohydrochloride.

What is claimed is:

1. An aqueous, pharmaceutical composition comprising, as an active ingredient, cinchonine dihydrochloride having a purity of at least 95%, in an aqueous carrier.

2. The composition of claim 1, wherein said cinchonine dihydrochloride is present in a purity of at least 99%.

3. The composition of claim 1, wherein said cinchonine dihydrochioride has a purity of at least 99.9%.

4. A method for treating multiple drug resistance phenomenon in an individual comprising administering an effective amount of the composition of claim 27 to said individual in need of amelioration of multiple drug resistance phenomenon.

* * * * *

UNITED STATES PATENT AND TRADEMARK OFFICE
CERTIFICATE OF CORRECTION

PATENT NO. : 6,528,524 B2
DATED : March 4, 2003
INVENTOR(S) : Philippe Genne et al.

It is certified that error appears in the above-identified patent and that said Letters Patent is hereby corrected as shown below:

Column 6,
Lines 8 and 14, "dihydrochioride" should read -- dihydrochloride --.
Line 17, "claim 27" should read -- claim 1 --.

Signed and Sealed this

Fifth Day of August, 2003

JAMES E. ROGAN
*Director of the United States Patent and Trademark Office*